United States Patent
Song et al.

(10) Patent No.: US 8,438,979 B2
(45) Date of Patent: May 14, 2013

(54) MEDICAL INSTRUMENT

(75) Inventors: Mi Ran Song, Seoul (KR); Jae-Gyoung Kim, Seoul (KR); Young Seuk Song, Seoul (KR); Sun ki Lee, Seoul (KR); Soo-Hwan Shin, Seoul (KR)

(73) Assignee: Medison Co., Ltd., Gangwon-do (KR)

( * ) Notice: Subject to any disclaimer, the term of this patent is extended or adjusted under 35 U.S.C. 154(b) by 904 days.

(21) Appl. No.: 12/406,169

(22) Filed: Mar. 18, 2009

(65) Prior Publication Data

US 2010/0000447 A1    Jan. 7, 2010

(30) Foreign Application Priority Data

Jul. 3, 2008    (KR) .................. 10-2008-0064562

(51) Int. Cl.
*A47B 37/00* (2006.01)
(52) U.S. Cl.
USPC ...................... 108/50.01; 312/209
(58) Field of Classification Search ........... 108/50.01, 108/50.02, 50.11, 43, 44; 312/209; 248/177.1, 248/680, 500, 506, 510, 346.07; 280/47.34, 280/47.35, 79.11
See application file for complete search history.

(56) References Cited

U.S. PATENT DOCUMENTS

| | | | | |
|---|---|---|---|---|
| 3,821,936 A * | 7/1974 | Morse | | 108/43 |
| 5,169,114 A * | 12/1992 | O'Neill | | 248/551 |
| 5,673,628 A * | 10/1997 | Boos | | 108/44 |
| 5,751,548 A | 5/1998 | Hall et al. | | |
| 5,847,924 A | 12/1998 | Youn | | |
| 6,722,673 B1 * | 4/2004 | Hamlin | | 280/47.35 |
| 7,823,844 B2 * | 11/2010 | Carnevali | | 248/176.1 |
| 2001/0000447 A1 | 4/2001 | Thompson | | |
| 2002/0181193 A1 | 12/2002 | Amemiya | | |
| 2003/0217940 A1 | 11/2003 | Russell | | |
| 2004/0007649 A1 | 1/2004 | Vettraino | | |
| 2004/0043650 A1 | 3/2004 | Yang et al. | | |
| 2006/0054751 A1 * | 3/2006 | Johnson et al. | | 248/123.11 |
| 2006/0176661 A1 | 8/2006 | Allen | | |
| 2007/0034753 A1 * | 2/2007 | Lee | | 248/121 |
| 2007/0131825 A1 * | 6/2007 | Skrodzki | | 248/177.1 |
| 2007/0140475 A1 | 6/2007 | Kurtock | | |
| 2007/0145219 A1 * | 6/2007 | Lin | | 248/274.1 |
| 2008/0035029 A1 * | 2/2008 | Adams | | 108/50.02 |
| 2009/0090839 A1 * | 4/2009 | Lin | | 248/676 |

FOREIGN PATENT DOCUMENTS

| | | |
|---|---|---|
| EP | 1176494 A1 | 1/2002 |
| JP | 2005-143734 | 6/2005 |
| KR | 10-0176645 B1 | 11/1998 |
| KR | 10-0303671 B1 | 7/2001 |
| KR | 10-2004-0020153 A | 3/2004 |

OTHER PUBLICATIONS

Korean Office Action issued in Korean Patent Application No. 10-2008-0064562, dated Jul. 27, 2011.

* cited by examiner

*Primary Examiner* — Hanh V Tran
*Assistant Examiner* — Andres F Gallego
(74) *Attorney, Agent, or Firm* — McDermott Will & Emery LLP (57) ABSTRACT

A medical instrument includes a main body including at least one of an operation part and a display part, and a detachable lever arranged on a rear portion of the main body, a cart including a desk on which the main body is positioned, a front detachable member disposed on the desk and adapted to attach and detach a front portion of the main body to/from the desk, and a rear detachable member disposed on the desk and adapted to attach and detach a rear portion of the main body to/from the desk and fix the main body to the desk by the detachable lever.

7 Claims, 11 Drawing Sheets

MEDICAL INSTRUMENT

CROSS-REFERENCE TO RELATED APPLICATION

This application claims the benefit of Korean Patent Application No. 10-2008-0064562, filed on Jul. 3, 2008, in the Korean Intellectual Property Office, the disclosure of which is incorporated herein by reference.

BACKGROUND OF THE INVENTION

1. Field of the Invention

The present invention relates to a medical instrument, and particularly, to a medical instrument in which a main body of the medical instrument is easily mounted to or separated from a cart.

2. Description of Related Art

In general, medical instruments are devices used in conducting diagnosis or medical treatment of patients in hospitals or physicians' offices. These medical instruments may be useful to doctors, and allow the doctors to more easily and accurately conduct the diagnosis or medical treatment. With development in techniques, current medical instruments may show a trend of improving performance and convenience, getting smaller, and the like. In particular, when the medical instruments are getting smaller, a high space utilization of the hospital may be acquired due to a reduction in occupied areas of the medical instruments, and convenience of use of the medical instruments may increase due to being easily movable and operated.

However, a conventional medical instrument may have limitations in its use convenience and miniaturization due to peripheral equipments even though the main body practically conducting medical treatments is relatively small in its size. As a representative example of the peripheral equipments, a structure used for supporting and moving the main body, controlling a height of the main body, and the like, or a storage for safekeeping accessories and consumption goods of the main body may be given. Accordingly, due to the limitation in miniaturization of the conventional medical instruments, a number of medical instruments may be used only in a separate consultation room, operating room, and the like. Also, disadvantageously, results of medical tests conducted using the medical instruments may be outputted as separate documents, photos, and the like, and provided to a doctor and a patient. Also, since the medical instruments may be difficult to be moved to the patient, high quality medical services are difficult to be acquired during medical services are provided at patients' residence.

A medical instrument of the present invention in which a main body practically conducting medical treatment may be easily mounted to and separated from a cart is disclosed.

A medical instrument of the present invention in which a detachable lever of the main body used for fixing a rear portion of the main body to a desk may be utilized as a handle to thereby enable common use of parts is disclosed.

A medical instrument of the present invention in which the main body separated from the medical instrument may be movable to various locations during ambulatory care to thereby conduct high quality medical services, and also to easily utilize data stored in the main body is disclosed.

SUMMARY OF THE INVENTION

An aspect of the present invention is to provide a medical instrument in which a main body practically conducting medical treatments may be easily mounted to and separated from a cart is disclosed.

Another aspect of the present invention is to provide a medical instrument in which a detachable lever of the main body used for fixing a rear portion of the main body to a desk may be utilized as a handle to thereby achieve common use of parts is disclosed.

Still another aspect of the present invention is to provide a medical instrument in which the main body separated from the medical instrument may be movable to various locations during ambulatory care to thereby conducting high quality medical services, and also easily utilize data stored in the main body is disclosed.

According to an aspect of the present invention, there is provided a medical instrument, including: a main body including at least one of an operation part and a display part, and a detachable lever arranged on a rear portion of the main body; a cart including a desk on which the main body is positioned; a front detachable member disposed on the desk and adapted to attach and detach a front portion of the main body to/from the desk; and a rear detachable member disposed on the desk and adapted to attach and detach a rear portion of the main body to/from the desk and fix the main body to the desk by the detachable lever. In this instance, the detachable lever may include a handle formed on the rear portion of the main body.

Also, the front detachable member may include: at least one first front fixing part upwardly protruded from a front portion of the desk and adapted to support a front side and both sides of the main body; and a second front fixing part movably arranged on the desk and adapted to closely contact an upper side of the main body with a side of the second front fixing part. Also, the side of the second front fixing part may be shaped to conform to the upper side and front side of the main body, so that the side of the second front fixing part is closely contacted with the upper side and front side of the main body.

Also, the detachable lever may be rotatably arranged on the rear portion of the main body, and the rear detachable member may include: at least one first rear fixing part formed on the rear portion of the desk and adapted to prevent interference with the detachable lever; a second rear fixing part formed on the at least one first rear fixing part so as to face a rear side of the main body; and a third rear fixing part movably arranged on the second rear fixing part and closely contacting with the rear portion of the main body when the main body is mounted on the desk.

In this instance, the first rear fixing part may be respectively disposed on a left and right side of the detachable lever.

Also, the third rear fixing part may include a fastening portion movably fastened on the second rear fixing part along the front and rear direction, and a contacting portion disposed on a side of the fastening portion and closely contacting with the rear side of the main body. Also, a rubber pad may be disposed on at least one of the contacting portion and the first rear fixing part, and the rubber pad is formed to face the main body.

According to another aspect of the present invention, the detachable lever may be arranged on the rear side of the main body to be protruded backwards, and the rear detachable member may include a detachable lever-insertion part into which the detachable lever is inserted and faces the rear side of the main body. In this instance, the detachable lever-insertion part may be formed to have the same width and height as those of the detachable lever so as to prevent vertical and horizontal movement of the detachable lever.

According to still another aspect of the present invention, the detachable lever may be rotatably arranged on the rear portion of the main body, and the rear detachable member may be curvedly protruded from the rear portion of the desk along a moving path of a latching groove formed on both sides of the detachable lever, the moving path of the latching groove being obtained by rotating the detachable lever, so that the rear detachable member is inserted in the latching groove. In this instance, the latching groove may be formed into a shape of a curved line having the same curvature as that of the rear detachable member.

According to yet another aspect of the present invention, the detachable lever may be rotatably arranged on the rear portion of the main body, and the rear detachable member may include: at least one first rear fixing part protruded from the rear portion of the desk and adapted to prevent interference with the detachable lever; a second rear fixing part formed on the at least one first rear fixing part so as to enable the rear portion of the main body to be seated on the second rear fixing part; and a third rear fixing part arranged on the second rear fixing part and adapted to prevent rotation of the detachable lever disposed on the lower portion of the first rear fixing part. In this instance, the first rear fixing part may be respectively disposed on a left and right side of the detachable lever. Also, the third rear fixing part may be rotatably arranged on the second rear fixing part, and include a latching protrusion formed on a side thereof so as to enable the detachable lever to be latched to the latching protrusion along a rotation angle of the third rear fixing part.

According to a further aspect of the present invention, the detachable lever may be rotatably arranged on the rear portion of the main body, and the rear detachable member may include: at least one first rear fixing part protruded from the rear portion of the desk and adapted to prevent interference with the detachable lever; and a second rear fixing part arranged on the at least one first rear fixing part so as to enable the detachable lever rotating below the first rear fixing part to be latched on the second rear fixing part. In this instance, the rear fixing part may be respectively arranged on left and right sides of the detachable lever.

Also, the second rear fixing part may be made of an elastic material, downwardly protruded from a bottom surface of the first rear fixing part, and include a detachable lever latching groove formed on a middle portion of a lower portion of the second rear fixing part and adapted for enabling the detachable lever to be inserted in the detachable lever latching groove.

BRIEF DESCRIPTION OF THE DRAWINGS

The above and/or other aspects and advantages of the present invention will become apparent and more readily appreciated from the following detailed description, taken in conjunction with the accompanying drawings of which.

DETAILED DESCRIPTION OF EXEMPLARY EMBODIMENTS

Reference will now be made in detail to exemplary embodiments of the present invention, examples of which are illustrated in the accompanying drawings, wherein like reference numerals refer to the like elements throughout. The exemplary embodiments are described below in order to explain the present invention by referring to the figures.

Figure 1:
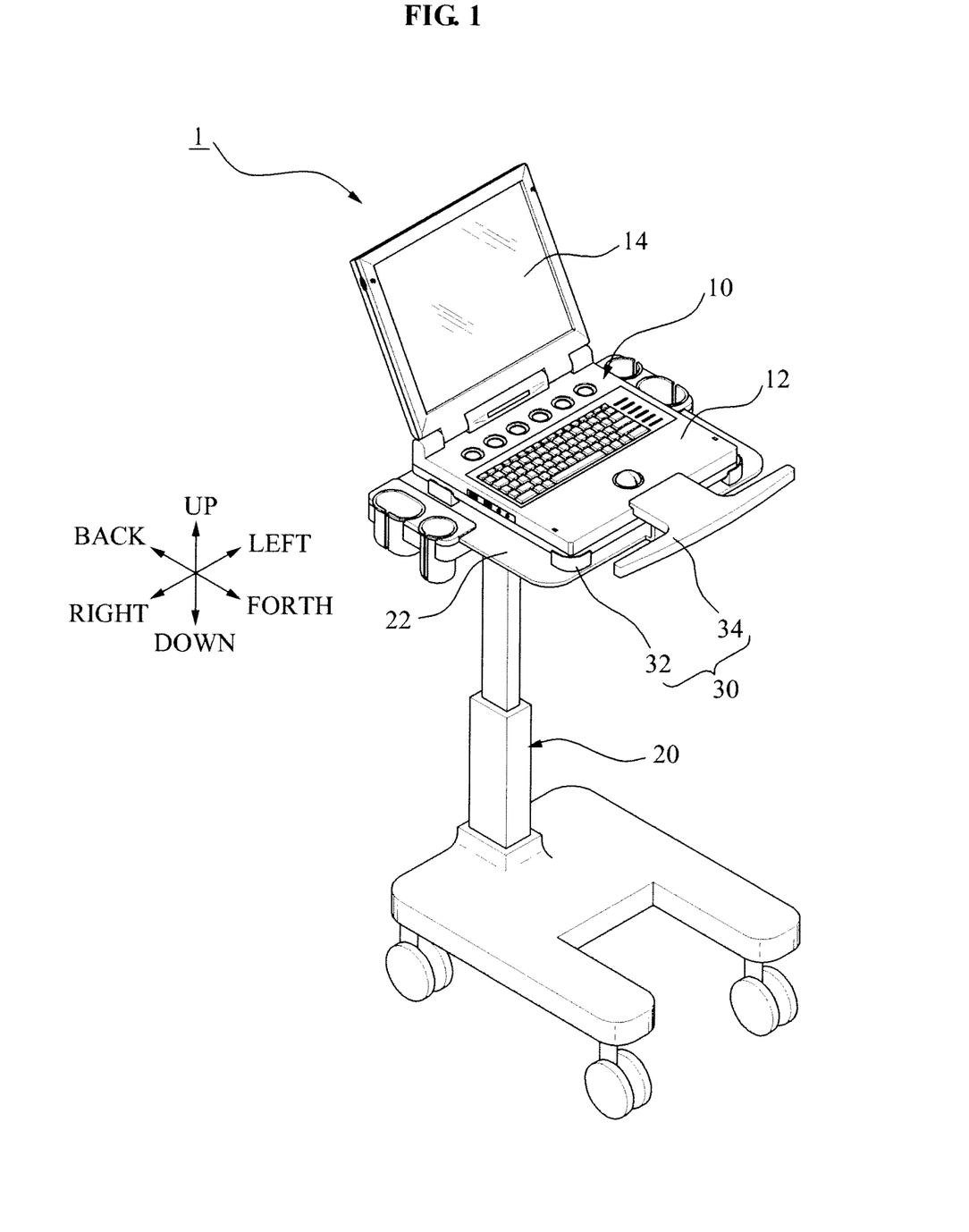
FIG. 1 is a perspective view showing a medical instrument according to an exemplary embodiment of the present invention.
Figure 2:
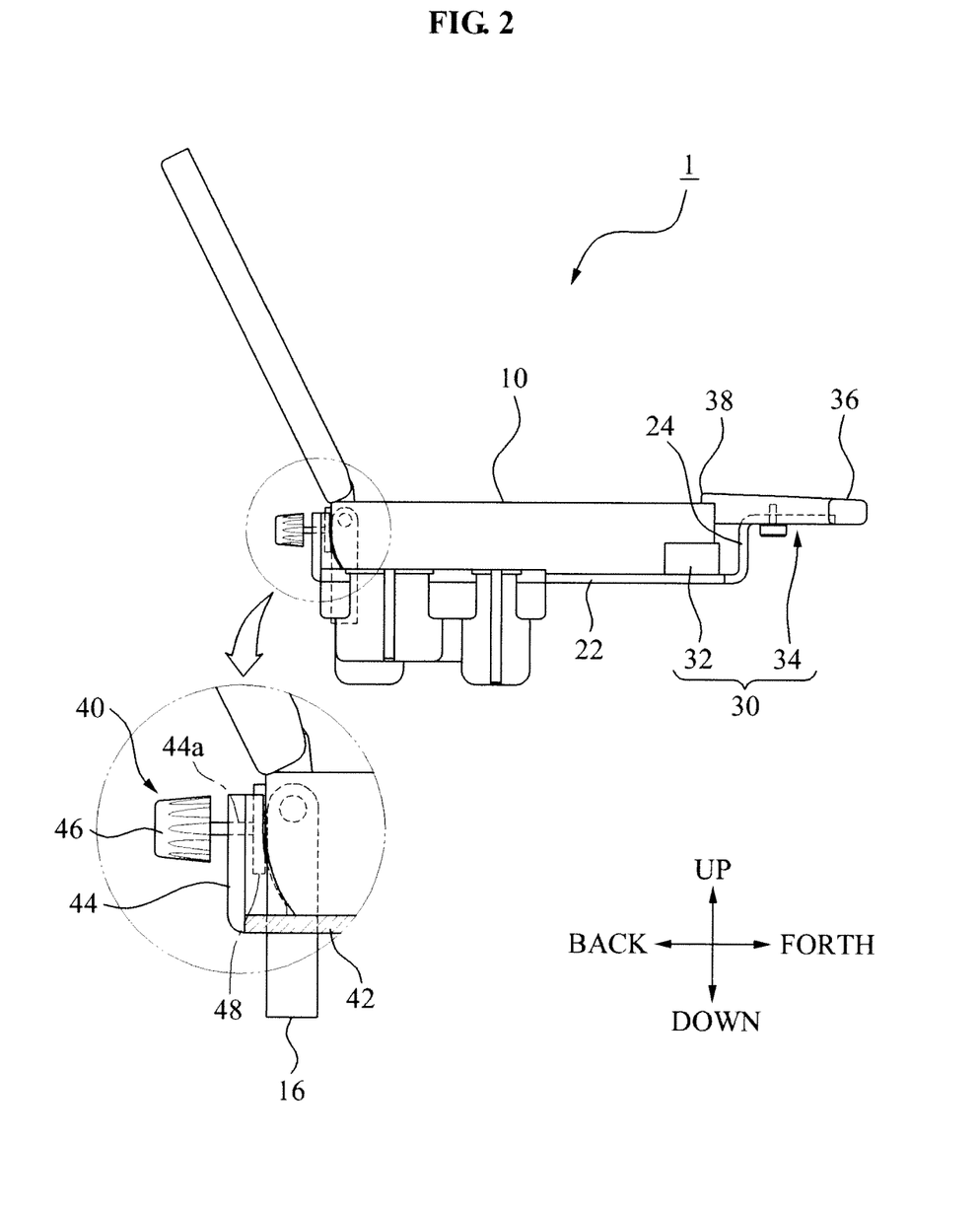
FIG. 2 is a side view showing a main body and desk of the medical instrument of FIG. 1.
Figure 3:
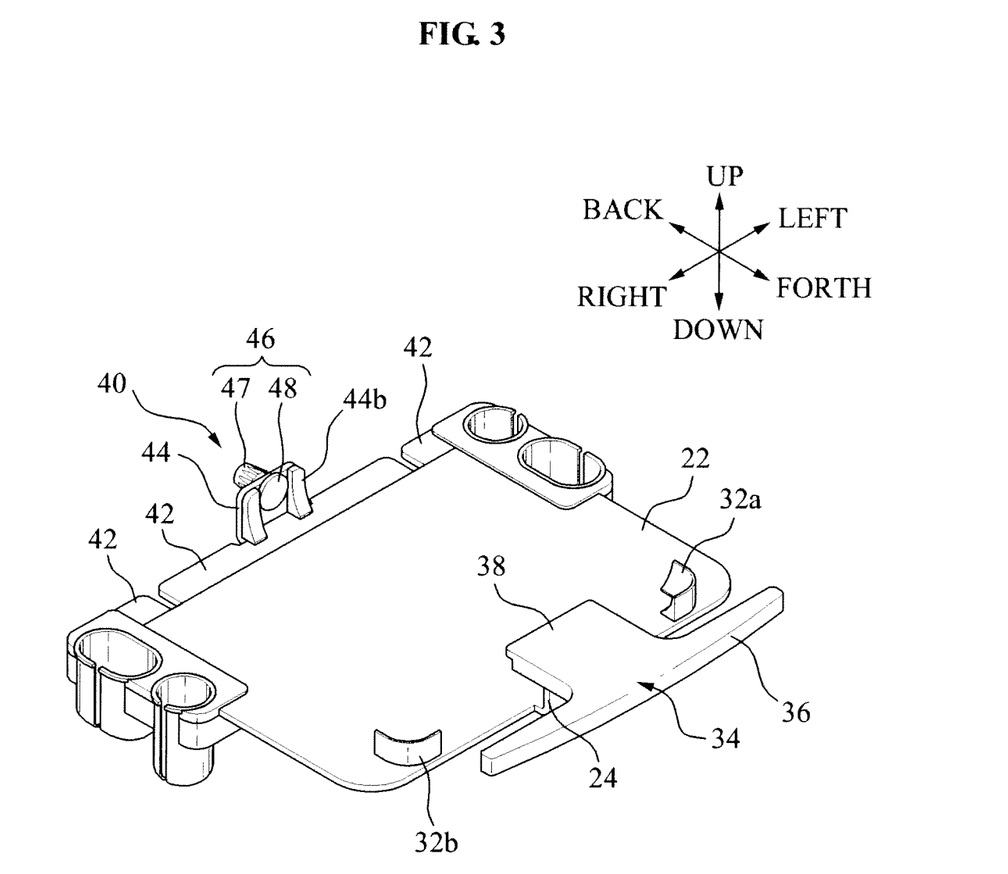
FIG. 3 is a perspective view showing the desk of the medical instrument of FIG. 1.

FIG. 1 is a perspective view showing a medical instrument 1 according to an exemplary embodiment of the present invention, FIG. 2 is a side view showing a main body and desk of the medical instrument of FIG. 1, and FIG. 3 is a perspective view showing the desk of the medical instrument of FIG. 1.

Referring to FIGS. 1 and 2, the medical instrument 1 of the present exemplary embodiment may include a main body 10 for practically conducting medical treatments and including a detachable lever 16 formed on a rear portion thereof to be vertically rotated, a cart 20 including a desk 22 on which the main body 10 is positioned, a front detachable member 30 disposed on the desk and adapted to attach and detach a front portion of the main body 10 to/from the desk 22, and a rear detachable member 40 disposed on the desk and adapted to attach and detach a rear portion of the main body 10 to/from the desk 22 and fix the main body to the desk.

Referring to FIGS. 1 and 2, the main body 10 may include at least one of an operation part 12 and a display part 14. The operation part 12 may be a part where signals for adjusting various setting, operations, and the like are inputted. The display part 14 may be a part where contents inputted in the operation part 12, operation state of the main body 10, diagnosis results obtained by using the main body, and the like are displayed. Hereinafter, the main body 10 including both of the operation part 12 and the display part 12 will be described in detail. Also, the detachable lever 16 may include a handle formed on the rear portion of the main body 10 to increase portability of the main body 10. Hereinafter, the detachable lever 16 that simultaneously acts as a handle and is connected at its both ends with the rear portion of the main body 10 in such a manner as to be vertically rotated will be described in detail.

Referring to FIGS. 1 to 3, the front detachable member 30 may include at least one first front fixing part 32 upwardly protruded from a front portion of the desk 22 and adapted to support a front side and both sides of the main body 10, and a second front fixing part 34 movably arranged on the desk 22 and adapted to closely contact an upper side of the main body 10 with a side of the second front fixing part, thereby fixing the front portion of the main body 10 to the desk 22.

The at least one first front fixing part 32 may include protruded ribs on left and right sides of the desk 22. Specifically, the at least one first front fixing part 32 may include a left rib 32a closely contacting with a front and left side surface of the main body 10, and a right rib 32b closely contacting with a front and right side surface of the main body 10. The second front fixing part 34 may include a location control part 36 coupled with a guide 24 formed on a front portion of the desk 22 and moved back and forth along the guide 24, and a latching part 38 backwardly protruded from the location control part 36 and closely contacting with an upper surface of the main body 10. The location control part 36 is arranged on an upper surface of the guide 24 and movably back and forth. The location control part 36 may be fixed by a coupling member of the guide 24. The guide 24 may include a slot formed thereon in a back and forth direction and adapted to be coupled with the coupling member. The coupling member may include a bolt coupled with the slot of the guide 24 and the location control part 36. The latching part 38 is protruded from a rear portion of the location control part 36 to a front portion of the main body 10. An end portion of the latching part 38 may be formed into a '⌐'-shape to conform to shapes of the upper and front surface of the main body 10, so that the end portion of the latching part 38 is in close contact with the upper and front surface of the main body 10 at the same time.

Referring to FIGS. 2 and 3, the rear detachable member 40 may include at least one first rear fixing part 42 formed on the rear portion of the desk 22 and adapted to prevent interference with the detachable lever 16, a second rear fixing part 44 formed on the at least one first rear fixing part 42 so as to face a rear side of the main body 10, and a third rear fixing part 46 movably arranged on the second rear fixing part 44 and closely contacting with the rear portion of the main body 10 when the main body is mounted to the desk.

The at least one first rear fixing part 42 may be backwardly protruded from the rear portion of the desk 22, and arranged on a location to prevent the interference with the detachable lever 16 when the detachable lever 16 is rotated. The at least one first rear fixing part 42 according to the present exemplary embodiment that is respectively arranged on left side, right side, and middle portion of the rear portion of the desk 22 will be herein described in detail. The at least one first rear fixing part 42 may be arranged adjacent to both ends of the detachable lever 16 to prevent horizontal movement of the detachable lever 16.

The second rear fixing part 44 is upwardly protruded from a rear portion of the first rear fixing part 42, so that the second rear fixing part 44 is spaced apart from a rear surface of the main body 10 by a certain distance. The second rear fixing part 44 may include a coupling hole 44a to correspond to the rear surface of the main body 10. A rubber pad 44b may be arranged on a front surface of the second rear fixing part 44 to prevent damage of the main body 10. The rubber pad 44b may be formed on remaining portions from the front surface of the second rear fixing part 44 where the coupling hole 44a is formed.

The third rear fixing part 46 may include a coupling part 47 coupled with the coupling hole 44a in such a manner as to be movable back and forth, and a contacting portion 48 formed on a surface of the coupling part 47 and closely contacting with the rear surface of the main body 10. The coupling part 47 may include a bolt inwardly passing through the coupling hole 44a. The contacting portion 48 may include a compression plate formed on an end of the coupling part 47 passing through the coupling hole 44a and arranged parallel to the rear surface of the main body 10. The contacting portion 48 may further include a rubber pad formed on an outer surface thereof to prevent damage to the main body 10.

A process in which the main body 10 is attached to and detached from the medical instrument 1 of the present exemplary embodiment configured as described above will be herein described.

The main body 10 may be attached to the medical instrument 1 in such a manner that the main body 10 is seated on the desk 22 of the cart 20 to be positioned between the first front fixing part 32 and the second rear fixing part 44, the front portion of the main body 10 is fixed on the desk 22 using the second front fixing part 34, and the rear portion of the main body 10 is fixed on the desk 22 using the detachable lever 16, the first rear fixing part 42, and the third rear fixing part 46. Accordingly, the medical instrument 1 may be more easily used in hospitals and the like, since the main body 10 may be movable with the cart 20. Hereinafter, a process in which the main body 10 is mounted on the desk 22 will be described in detail.

First, the main body 10 may be disposed between the first front fixing part 32 and the second rear fixing part 44, so that the first front fixing part 32 supports the front surface and both side surfaces of the main body 10, and the first rear fixing part 42 supports the rear surface of the main body 10. Specifically, the left rib 32a of the first front fixing part 32 supports the front surface and left side surface of the main body 10 to thereby prevent the main body 10 to be moved to the left and front, and the right rib 32b of the first front fixing part 32 supports the front surface and right side surface of the main body 10 to thereby prevent the main body 10 to be moved to the right and front. Also, the second rear fixing part 44 may support the rear surface of the main body 10 to thereby prevent the main body 10 to be moved to the back. Thus, the first front fixing part 32 and the second rear fixing part 44 may prevent the main body 10 to be moved forward, backward, right and left.

Next, the location control part 36 of the second front fixing part 34 is backwardly moved along the guide 24 of the desk 22, so that the latching part 38 of the second front fixing part 34 is in close contact with the front surface of the main body 10. The location control part 36 may be coupled and fixed on the guide 24 when the latching part 38 is in close contact with the front surface of the main body 10. Since the latching part 38 is in close contact with the upper surface of the main body 10, the front portion of the main body 10 is prevented from being upwardly separated from the first front fixing part 32. Also, since the latching part 38 is in close contact with the front surface of the main body 10, the latching part 38 may function to prevent the main body 10 from being separated from the desk 22 with the third rear fixing part 46

When the second rear fixing part 34 is completely mounted on the desk 22, the coupling part 47 is rotated in a direction in which the contacting portion 48 of the third rear fixing part 46 is forwardly moved, so that the contacting portion 48 of the third rear fixing part 46 is in close contact with the rear surface of the main body 10. As a result, the main body 10 may be arranged on the desk 22 in such a manner as to be sandwiched between the latching part 38 and the contacting portion 48. In particular, since the coupling part 47 has a configuration in which a bolt is coupled with the coupling hole 44a of the second rear fixing part 44, the latching part 38 and the contacting portion 48 may support the main body 10 via a load corresponding to a coupling force of the coupling part 47. Accordingly, the main body 10 may be significantly and stably fixed on the desk 22 by controlling the coupling force of the coupling part 47.

A process in which the main body 10 is separated from the desk 22 will be performed in reverse order of the process in which the main body 10 is mounted to the desk 22. Specifically, the coupling part 47 is backwardly moved so that the contacting portion 48 is separated from the rear surface of the main body 10, and the location control part 36 is forwardly moved so that the latching part 38 is separated from the front surface of the main body 10. When a state where the main body 10 is mounted on the desk 22 by the third rear fixing part 46 and the second front fixing part 34 is released, the main body 10 positioned between the first front fixing part 32 and the second rear fixing part 44 may be upwardly separated from the desk 22. As a result, the main body 10 may be movable to various locations, and data stored in the main body 10 may be directly used.

Figure 4:
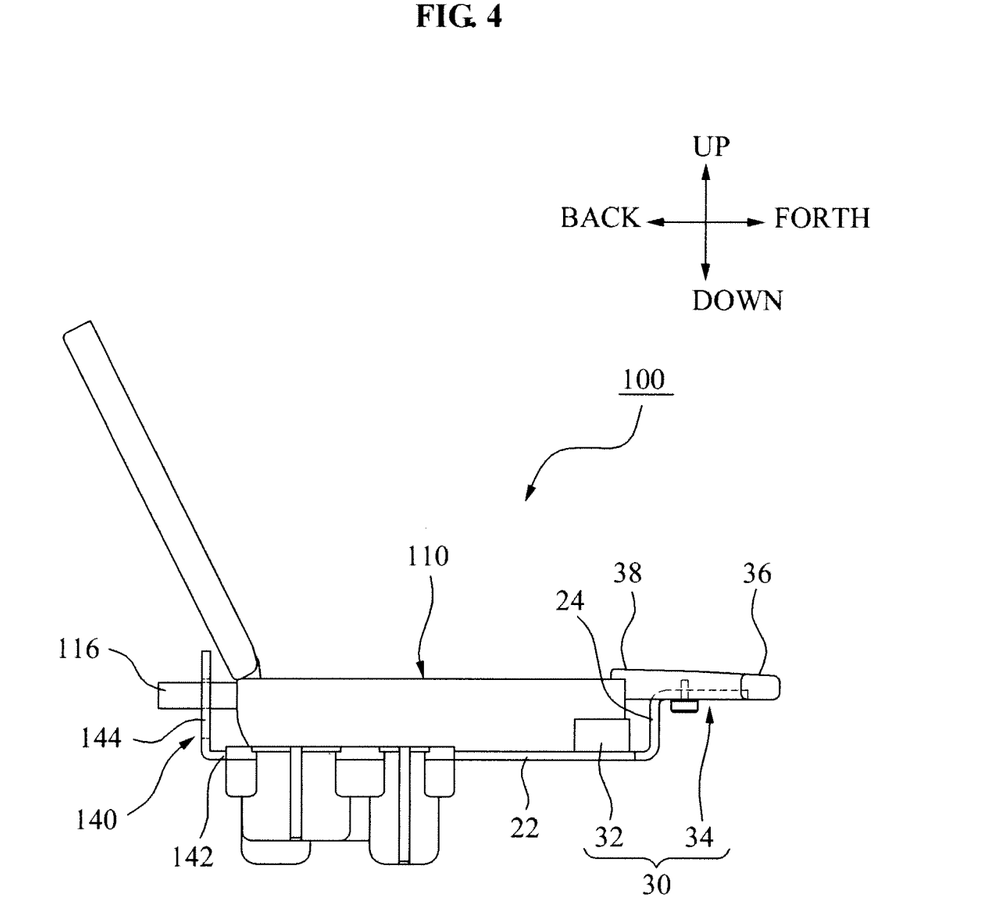
FIG. 4 is a side view showing a main body and desk of a medical instrument according to another exemplary embodiment of the present invention.
Figure 5:
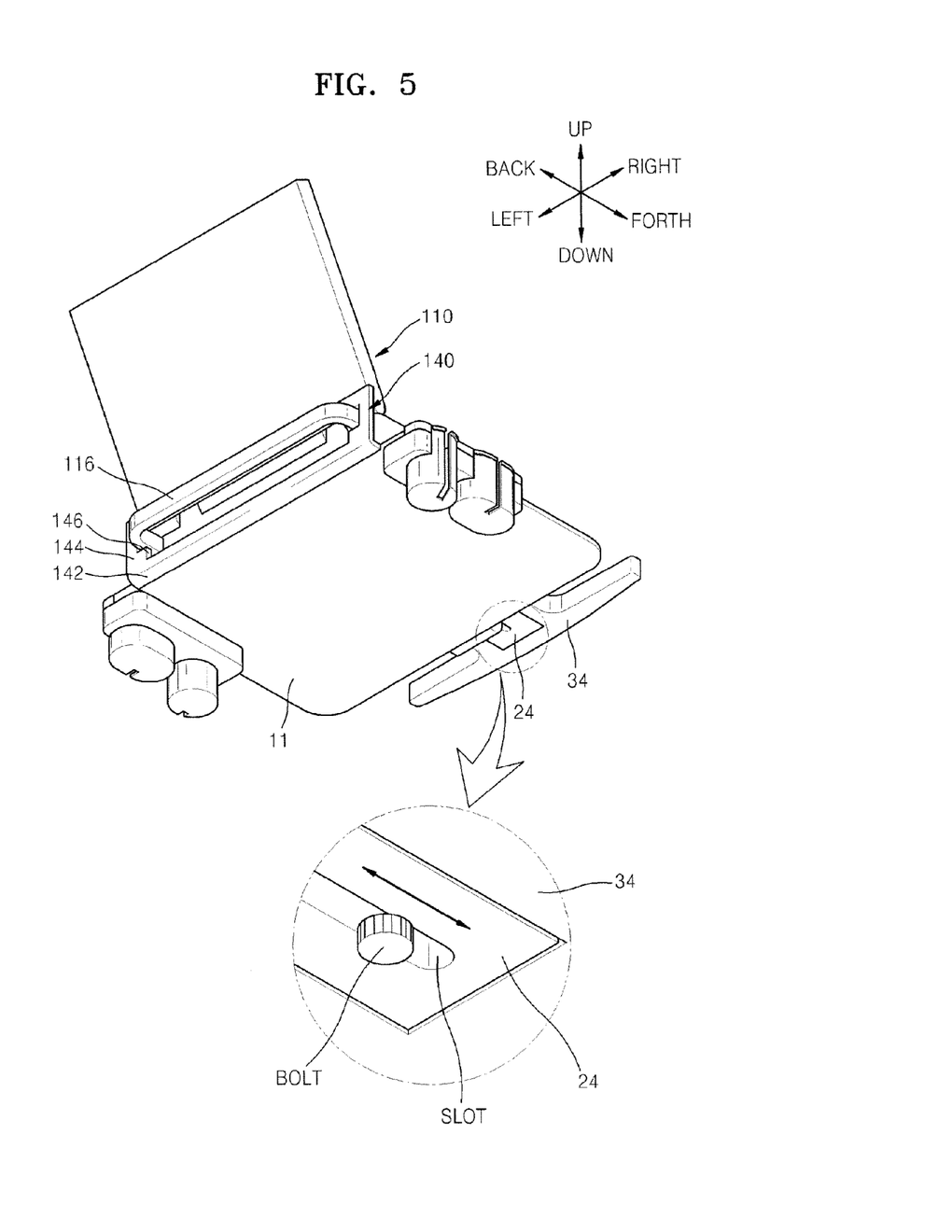
FIG. 5 is a perspective view showing main parts of a main body and desk of the medical instrument of FIG. 4.

FIG. 4 is a side view showing a main body and desk of a medical instrument 100 according to another exemplary embodiment of the present invention, and FIG. 5 is a perspective view showing main parts of a main body and a desk of the medical instrument of FIG. 4.

Identical reference numerals shown in FIGS. 4 and 5 and FIGS. 1 to 3 may denote identical components. Hereinafter, only components of the medical instrument 100 of FIGS. 4 and 5 which are different from those of the medical instrument 1 of FIGS. 1 to 3 will be described in detail. The main body 110 according to the present exemplary embodiment may include a detachable lever 116 backwardly protruded, and the desk 22 may include a rear detachable member 140 formed on a rear portion thereof to face a rear surface of the main body 110 and including a detachable lever-insertion part 146 for enabling the detachable lever 116 to be inserted therein.

The detachable lever 116 may include a handle formed on the rear portion of the main body 110 to increase portability of the main body 110. The detachable lever 116 may be rotatable or non-rotatable with respect to the rear portion of the main body 110, however, the detachable lever 116 according to the present exemplary embodiment may be non-rotatable with respect to the rear portion of the main body 110, and backwardly protruded.

The rear detachable member 140 may include a horizontal portion 142 horizontally and backwardly extended from the rear portion of the desk 22, and a vertical portion 144 vertically and upwardly extended from the horizontal portion 142. The horizontal portion 142 may be formed to have a length to interfere with the detachable lever 116 of the main body 110 seated on the desk 22 and the vertical portion 144. The vertical portion 144 may be arranged to correspond to the detachable lever 116. The detachable lever-insertion part 146 may be formed into a hole or groove shape on a middle portion of the vertical portion 144. Also, the detachable lever-insertion part 146 may be formed to have the same width and height as those of the detachable lever 116 so as to prevent vertical and lateral movement of the detachable lever 116. When the detachable lever-insertion part 146 is formed into a groove shape, the main body 110 may be stably fixed between the second front fixing part 34 and the detachable lever-insertion part 146 by means of a force by which the second front fixing part 34 is in close contact with the front portion of the main body 110. However, as shown in FIG. 5, the detachable lever-insertion part 146 according to the present exemplary embodiment which is formed into a hole shape will be described.

In the medical instrument 100 configured as described above, the rear portion of the main body 10 may be easily fixed to the desk 22 by a relatively simple operation such that the detachable lever 116 of the main body 110 is inserted into the detachable lever-insertion hole 146. Specifically, since the detachable lever 116 is latched on the detachable lever-insertion part 146 in a vertical and lateral direction, vertical and lateral movement of the rear portion of the main body 110 may be limited. Accordingly, the medical instrument 100 according to the present exemplary embodiment has a relatively simple structure and operation by which the rear portion of the main body 110 is fixed on the desk.

Figure 6:
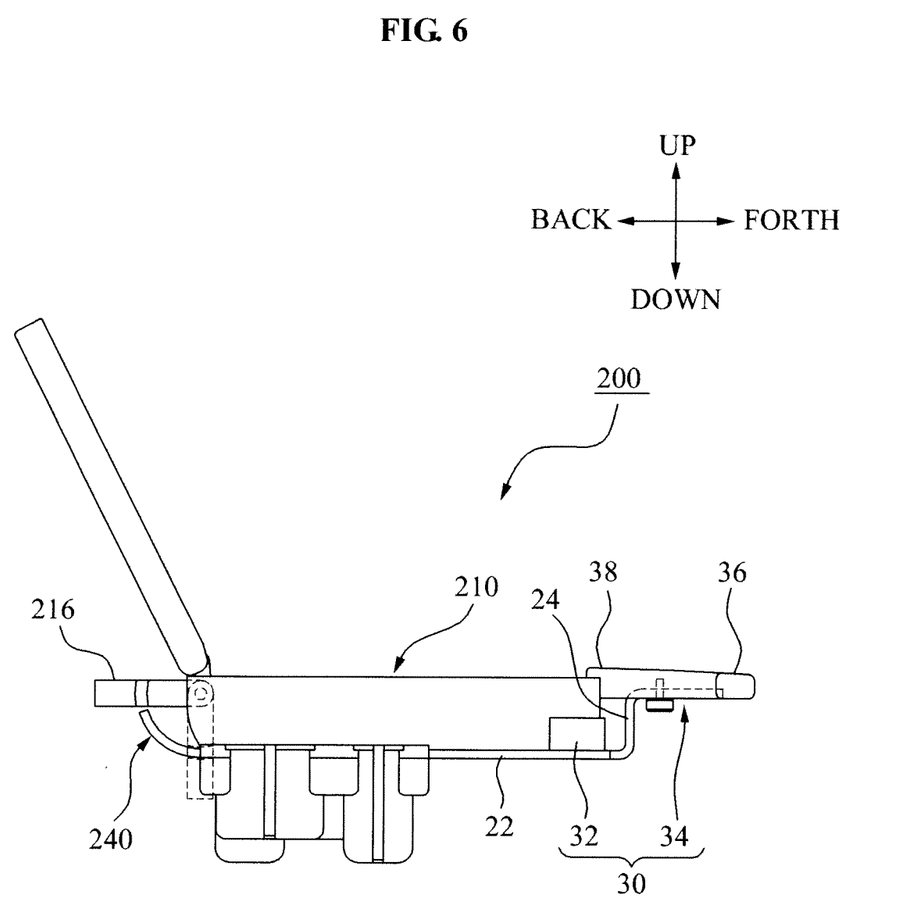
FIG. 6 is a side view showing a main body and desk of a medical instrument according to still another exemplary embodiment of the present invention.
Figure 7:
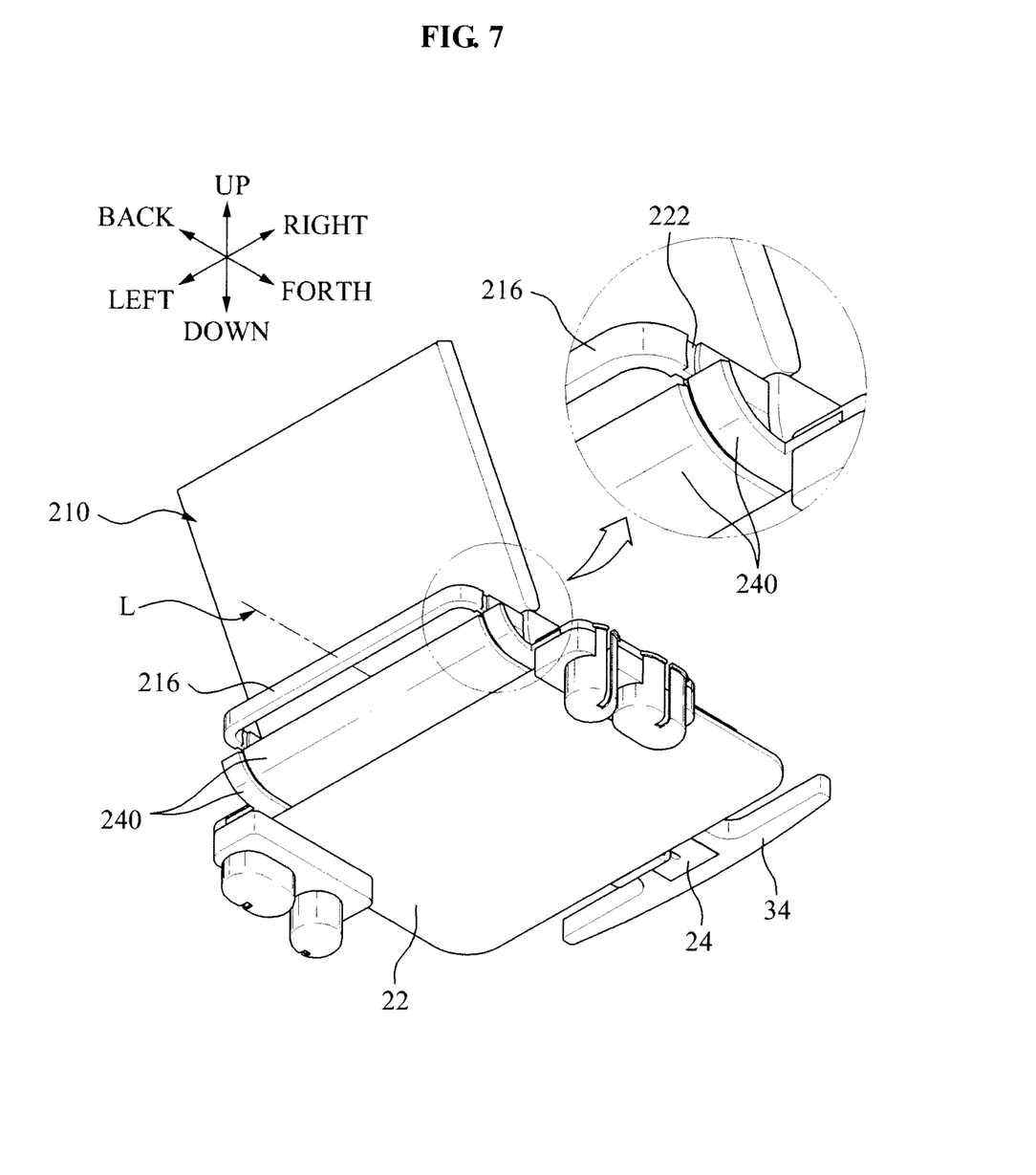
FIG. 7 is a perspective view showing main parts of a main body and desk of the medical instrument of FIG. 6.

FIG. 6 is a side view showing a main body and desk of a medical instrument 200 according to still another exemplary embodiment of the present invention, and FIG. 7 is a perspective view showing main parts of a main body and desk of the medical instrument of FIG. 6.

Identical reference numerals shown in FIGS. 6 and 7 and FIGS. 1 to 3 may denote identical components. Hereinafter, only components of the medical instrument 200 of FIGS. 6 and 7 which are different from those of the medical instrument 1 of FIGS. 1 to 3 will be described in detail.

A detachable lever 216 of a main body 210 may include a latching groove 222 respectively formed on both sides thereof, and a rear detachable member 240 is curvedly protruded from a rear portion of the desk 22 so that the rear detachable member 240 is inserted in the latching groove 222 when the detachable lever 216 is rotated.

Referring to FIG. 7, the detachable lever 216 may include a handle rotatably arranged on the rear portion of the main body 210 so as to increase portability of the main body 210. According to the present exemplary embodiment, the both ends of the detachable lever 216 are rotatably connected with left and right sides of the rear portion of the main body 210. The latching groove 222 may be formed into a shape of a curved line having the same curvature as that of the rear detachable member 240. The latching groove 222 may be symmetrically formed on the both ends of the detachable lever 216 with respect to an imaginary line (L) cutting a middle portion of the both ends of the detachable lever 216. Specifically, the latching groove 222 may be symmetrically formed on a left side surface of a left end of the detachable lever 216 and a right side surface of a right end thereof with respect to the imaginary line (L), or symmetrically formed on a right side surface of the left end of the detachable lever 216 and a left side surface of the right end thereof with respect to the imaginary line (L). However, the latching groove 222 according to the present exemplary embodiment which is symmetrically formed on the both side surfaces of the both ends of the detachable lever 216 with respect to the imaginary line (L) will be herein described.

The rear detachable member 240 may be curvedly protruded from the rear portion of the desk 22 along a moving path of the latching groove 222 when the detachable lever 216 is rotated. Accordingly, when the detachable lever 216 of the main body 210 seated on the desk 22 is downwardly rotated, the rear detachable member 240 is inserted in the latching groove 222, and the latching groove 222 is downwardly moved along the rear detachable member 240. A plurality of the rear detachable members 240 may be formed on the rear portion of the desk 22 so as to correspond to the latching groove 222 formed on the both ends of the detachable lever 216. Specifically, the rear detachable member 240 may be respectively disposed on left and right sides of the both ends of the detachable lever 216, so that the plurality of the rear detachable members 240 are respectively inserted in the latching groove 222. As shown in FIG. 7, the plurality of rear detachable members are respectively disposed on the right, left, and middle portion of the rear portion of the desk 22.

According to the medical instrument 200 configured as described above, the rear portion of the main body 210 is easily fixed on the desk 22 with a relatively simple operation such that the main body 210 is seated on the desk 22, and then the detachable lever 216 is downwardly rotated. Specifically, when the detachable lever 216 is downwardly rotated, vertical movement of the detachable lever 216 is limited by the latching groove 222 and the rear detachable member 240, and lateral movement of the detachable lever 216 is limited by the rear detachable member 240 respectively arranged on the left and right sides of the detachable lever 216. Because the rear detachable member 240 functions to limit the vertical and lateral movement of the detachable lever 216, the rear portion of the main body 210 is prevented from being vertically or laterally moved. Accordingly, the medical instrument 200 according to the present exemplary embodiment has a relatively simple structure and operation by which the rear portion of the main body 210 is fixed on the desk 22.

Figure 8:
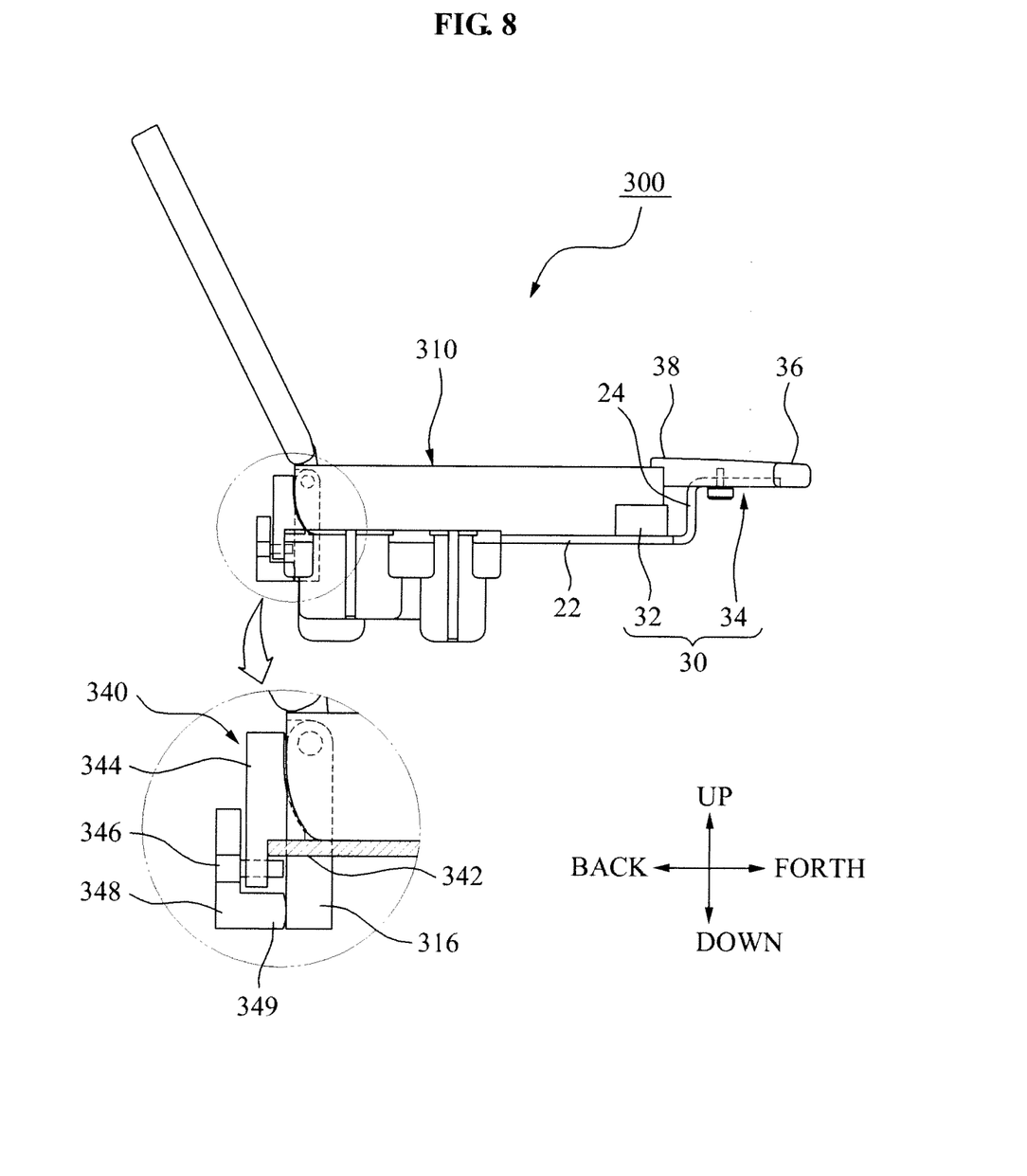
FIG. 8 is a side view showing a main body and desk of a medical instrument according to yet another exemplary embodiment of the present invention.
Figure 9:
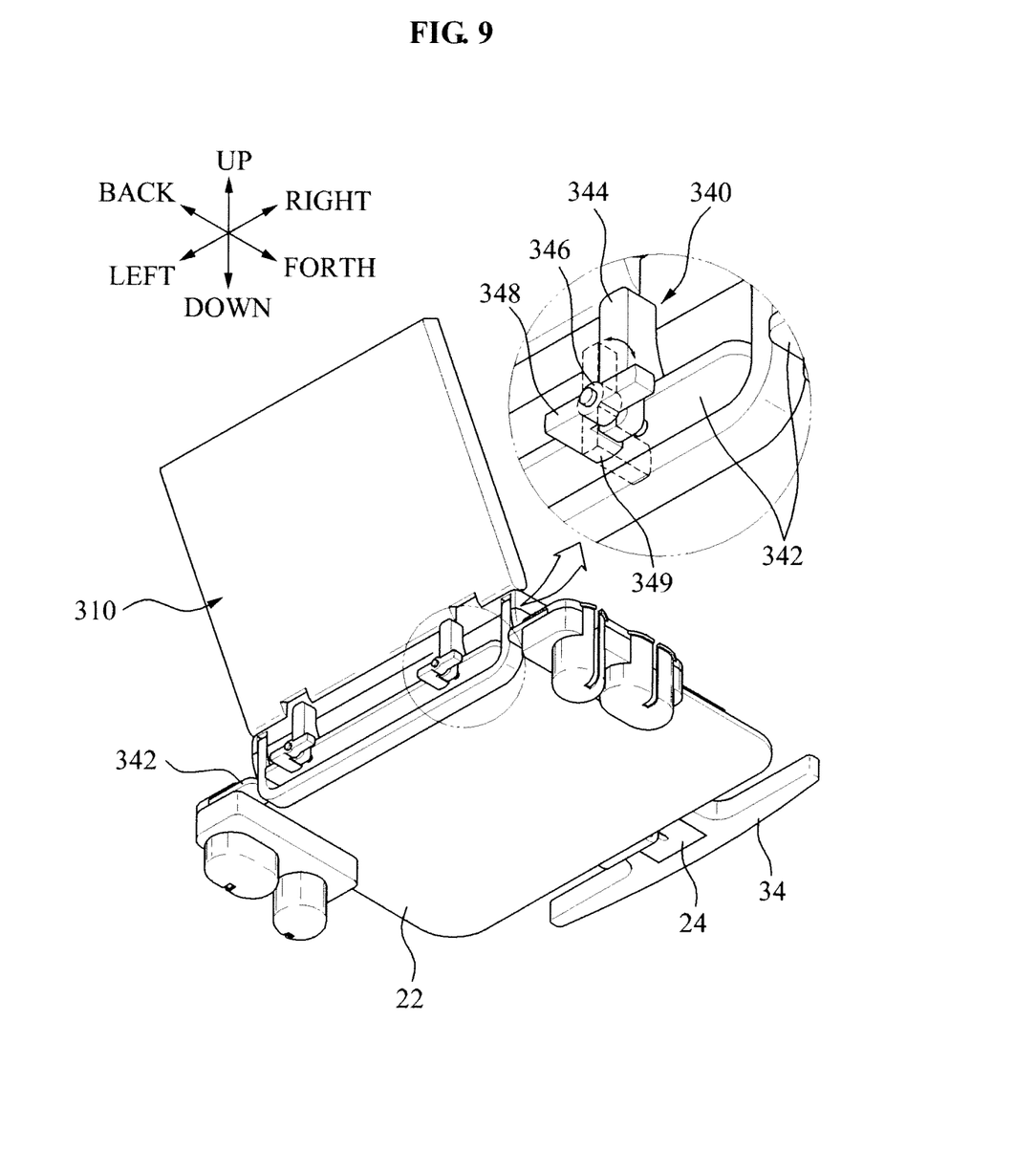
FIG. 9 is a perspective view showing main parts of a main body and desk of the medical instrument of FIG. 8.

FIG. 8 is a side view showing a main body and desk of a medical instrument 300 according to yet another exemplary embodiment of the present invention, and FIG. 9 is a perspective view showing main parts of a main body and desk of the medical instrument of FIG. 8.

Identical reference numerals shown in FIGS. 8 and 9 and FIGS. 1 to 3 may denote identical components. Hereinafter, only components of the medical instrument 300 of FIGS. 8 and 9 which are different from those of the medical instrument 1 of FIGS. 1 to 3 will be described in detail. In the medical instrument 300 according to the present exemplary embodiment, a rear detachable member 340 may include at least one first rear fixing part 342 formed on the rear portion of the desk 22, a second rear fixing part 344 formed on the at least one first rear fixing part 342, and a third rear fixing part 346 formed on the second rear fixing part 344 to prevent a detachable lever 316 of a main body 310 rotated below the first rear fixing part 342 from being upwardly rotated. The detachable lever 316 may include a handle formed on the rear portion of the main body 310 so as to increase portability of the main body 310. According to the present exemplary embodiment, both ends of the detachable lever 316 are rotatably connected with left and right sides of the rear portion of the main body 310.

The at least one first rear fixing part 342 may be backwardly protruded from the rear portion of the desk 22, and disposed on a location where interference with the detachable lever 316 is avoided when the detachable lever 316 is rotated. Referring to FIG. 9, the at least one first rear fixing part 342 according to the present exemplary embodiment may be respectively disposed on a left side, right side, and middle portion of the rear portion of the desk 22. The first rear fixing part 342 may be respectively disposed adjacent to the both ends of the detachable lever 316 so as to prevent lateral movement of the detachable lever 316.

The second rear fixing part 344 may be upwardly protruded from at least one of the first rear fixing parts 342. The second rear fixing part 344 may be formed to correspond to the rear portion of the main body 310 so that the rear portion of the main body 310 is stably disposed. As shown in FIG. 9, two second rear fixing parts 344 are arranged on left and right portions of the first rear fixing part 342 located in the middle portion of the rear portion of the desk 22, and spaced apart from each other by a certain distance.

The third rear fixing part 346 may be arranged on the second rear fixing part 344 in such a manner that a middle portion of the third rear fixing part 346 is rotatable. The third rear fixing part 346 may include a latching protrusion 348 extended in a radius direction from the middle portion. The latching protrusion 348 may be formed to have a length to be interfered or non-interfered with the detachable lever 316 having been rotated below the first rear fixing part 342 depending on a rotation angle of the third rear fixing part 346.

The third rear fixing part 346 may include a spacer forwardly protruded from an end of the latching protrusion 348 to correspond to the detachable lever 316 having been rotated below the first rear fixing part 342. The spacer 349 may be formed to have a length to be in close contact with the detachable lever 316 so that a space created between the latching protrusion 348 and the detachable lever having been rotated below the first rear fixing part 342 is removed.

According to the medical instrument 300 configured as described above, the rear portion of the main body 310 is easily fixed on the desk 22 with a relatively simple operation such that the detachable lever 316 of the main body 310 seated on the desk 22 is downwardly rotated, and the third rear fixing part 346 is rotated. Specifically, the main body 310 may not be separated from the desk 22 by the detachable lever 316 having been rotated below the first rear fixing part 342. Also, when the detachable lever 316 is rotated below the first rear fixing part 342, lateral movement of the detachable lever 316 may be limited by the plurality of first rear fixing parts 342. Accordingly, the rear portion of the main body 310 may be prevented from being laterally and vertically moved.

Figure 10:
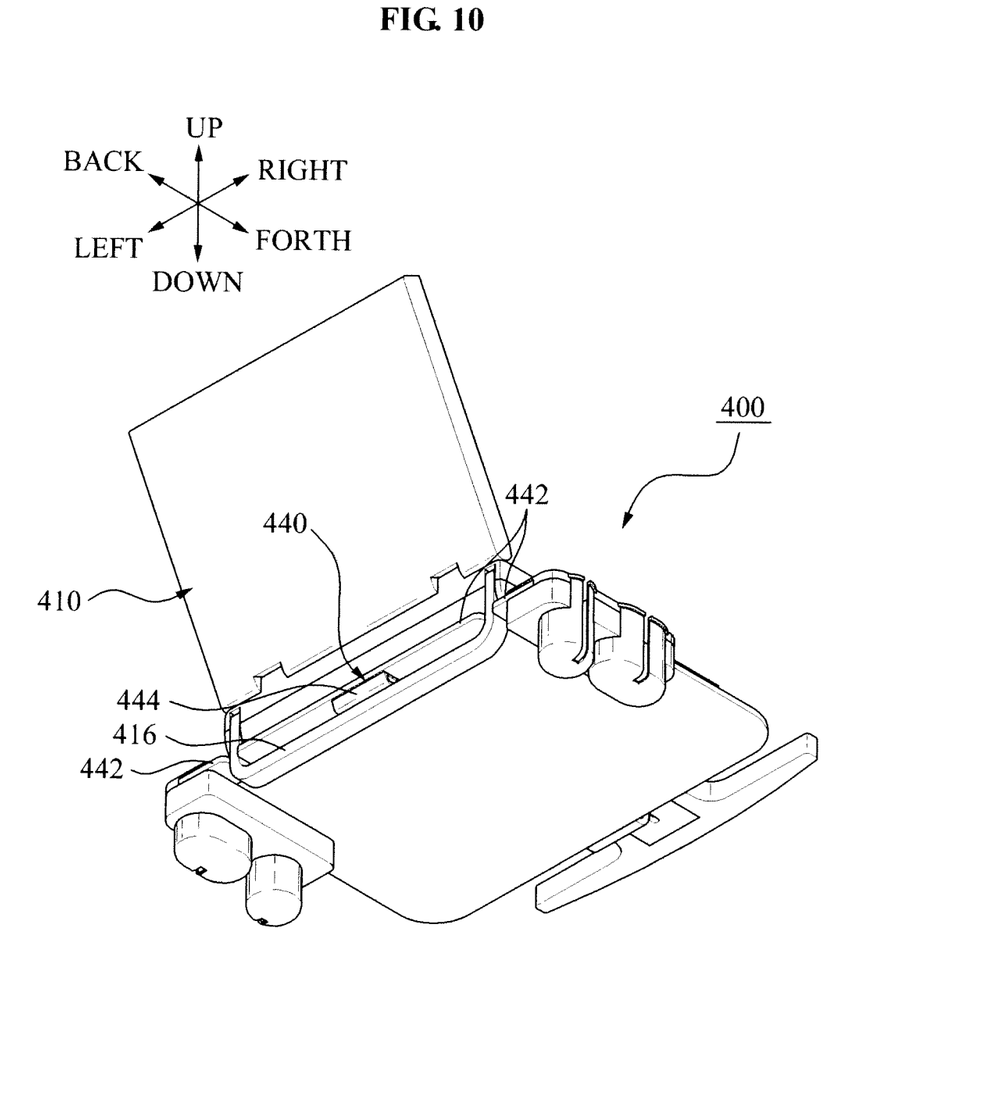
FIG. 10 is a perspective view showing a main body and desk of a medical instrument according to a further exemplary embodiment of the present invention.
Figure 11:
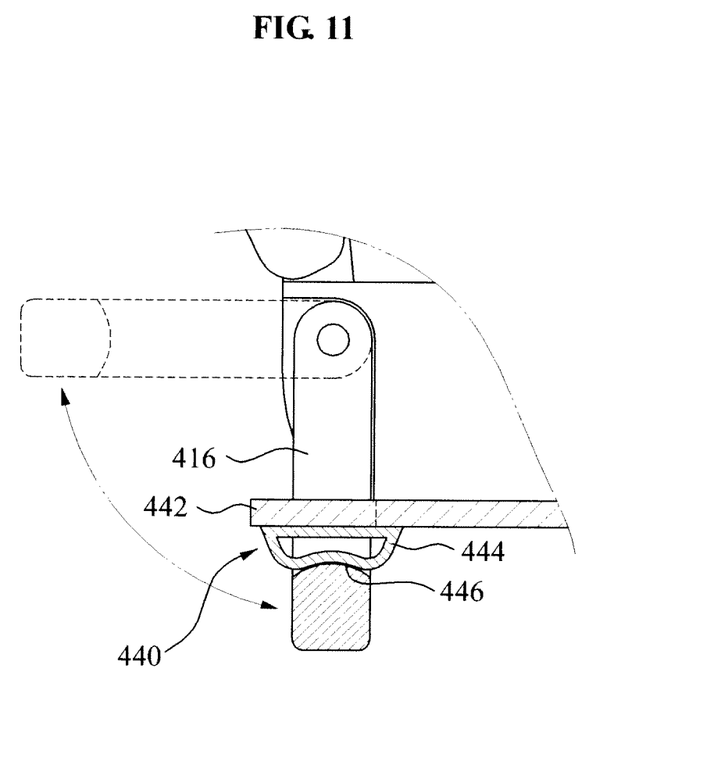
FIG. 11 is a cross-sectional view showing a detachable lever and a rear detachable member of the medical instrument of FIG. 10.

FIG. 10 is a perspective view showing a main body and desk of a medical instrument 400 according to a further exemplary embodiment of the present invention, and FIG. 11 is a cross-sectional view showing a detachable lever and a rear detachable member of the medical instrument of FIG. 10.

Identical reference numerals shown in FIGS. 10 and 11 and FIGS. 1 to 3 may denote identical components. Hereinafter, only components of the medical instrument 400 of FIGS. 10 and 11 which are different from those of the medical instrument 1 of FIGS. 1 to 3 will be described in detail. In the medical instrument 400 according to the present exemplary embodiment, a rear detachable member 440 may include at least one first rear fixing part 442 protruded from a rear portion of the desk 22, and a second rear fixing part 444 arranged on the at least one first rear fixing part 442 so as to enable the detachable lever 416 rotating below the first rear fixing part 442 to be latched on the second rear fixing part 444. The detachable lever 416 may include a handle rotatably formed on a rear portion of a main body 410 so as to increase portability of the main body 410. According to the present exemplary, both ends of the detachable lever 416 are connected with left and right sides of the rear portion of the main body 410 in such a manner that the detachable lever 416 is vertically rotated.

The at least one first rear fixing part 442 is backwardly protruded from the rear portion of the desk 22, and arranged on the rear portion of the desk 22 so that interference with the detachable lever 416 is avoided when the detachable lever 416 is rotated. Referring to FIG. 10, the at least one first rear fixing part 442 according to the present exemplary embodiment may be respectively arranged on left side, right side, and middle portion of the rear portion of the desk 22. The at least one first rear fixing part 442 may be arranged adjacent to both ends of the detachable lever 416 to prevent lateral movement of the detachable lever 416.

The second rear fixing part 444 may be made of an elastic material, and downwardly protruded from a bottom surface of the first rear fixing part 442. The second rear fixing part 444 may be made of a rubber, plate spring, and the like, excellent in elastic force. The second rear fixing part 444 according to the present exemplary is made of the rubber.

Referring to FIG. 10, the second rear fixing part 444 may be arranged on the bottom surface of the first rear fixing part 442 located in a middle portion of the rear portion of the desk 22, and may be formed to have a height to be interfered with the detachable lever 416 having been rotated below the first rear fixing part 442. The second rear fixing part 444 may include a detachable lever-latching groove 446 formed on a middle portion of a lower portion thereof and adapted for enabling the detachable lever 416 to be inserted in the detachable lever-latching groove 446. The detachable lever 416 may be formed into a shape conformed to a shape of the detachable lever-latching groove 416. According to the present exemplary embodiment, the detachable lever 416 and a corresponding surface of the detachable lever-latching groove 446 may be formed into a convex shape. As a result, the detachable lever 416 may smoothly advance in the detachable lever-latching groove 446 of the second rear fixing part 444. Referring to FIG. 11, the second rear fixing part 444 may be formed with a hollow inside so as to increase elastic deformation.

According to the medical instrument 400 configured as described above, the rear portion of the main body 410 is easily fixed on the desk 22 with a relatively simple operation such that the main body 410 is seated on the desk 22, and the detachable lever 416 of the main body 410 is downwardly rotated until the detachable lever 416 is inserted into the detachable lever-latching groove 446 of the second rear fixing part 444. Specifically, when the detachable lever 416 is rotated below the first rear fixing part 442, the detachable lever 416 is latched on a part of the lower portion of the second rear fixing part 444. Next, when the detachable lever 416 is further forcibly and downwardly rotated, the detachable lever 416 is forcibly moved to and inserted in the detachable lever-latching groove 446 while upwardly pushing the part of the lower portion of the second rear fixing part 444. When the detachable lever 416 is inserted in the detachable lever-latching groove 446, a location of the detachable lever 416 is fixed since the part of the lower portion of the second rear fixing part 444 is elastically restored. As a result, the main body 410 may not be separated from the desk 22 by the detachable lever 416 inserted in the detachable lever-latching groove 446, and lateral movement of the detachable lever 416 is limited by the plurality of first rear fixing parts 442 arranged on the both ends of the detachable lever 416. Specifically, the rear portion of the main body 410 may be prevented from being laterally or vertically moved.

As described above, according to the present invention, a main body may be easily mounted to and separated from a desk of a cart by a front detachable member and a rear detachable member, thereby improving utilization and convenience of use of a medical instrument, and also enabling simple maintenance and repair of the main body.

According to the present invention, a detachable lever of the main body used for fixing a rear portion of the main body to the desk may be utilized as a handle, thereby enabling common use of parts, and additionally simplifying a structure in which the rear portion of the main body is fixed to the desk.

According to the present invention, the main body separated from the medical instrument may be moved to a desired location to utilize data stored in the main body, thereby improving utilization of the data.

According to the present invention, the main body separated from the medical instrument may be moved to various locations other than hospitals to be used for diagnosis of patients, thereby more easily conducting ambulatory care.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A medical instrument, comprising:
    a cart including a desk on which a main body is positioned;
    a front detachable member disposed on the desk and adapted to attach and detach a front portion of the main body to/from the desk; and
    a rear detachable member disposed on the desk and adapted to attach and detach a rear portion of the main body to/from the desk and fix the main body to the desk by a detachable lever,
    wherein the front detachable member includes:
    at least two first front fixing parts upwardly protruded from a front portion of the desk and each adapted to support a front side and a lateral side of the main body; and
    a second front fixing part arranged on the desk movable toward and away from the desk, and adapted to closely contact an upper side of the main body with a side of the second front fixing part,
    wherein the main body includes at least one of an operation part and a display part, the detachable lever is arranged on the rear portion of the main body,
    wherein the detachable lever is rotatably arranged on the rear portion of the main body,
    wherein the rear detachable member includes:
    at least one first rear fixing part formed on a rear portion of the desk and adapted to prevent interference with the detachable lever;
    a second rear fixing part formed on the at least one first rear fixing part so as to face a rear side of the main body; and
    a third rear fixing part movably arranged on the second rear fixing part and closely contacting with the rear portion of the main body when the main body is mounted on the desk, and
    wherein the third rear fixing part includes a fastening portion movably fastened on the second rear fixing part along a front and rear direction, and a contacting portion disposed on a side of the fastening portion and closely contacting with the rear side of the main body.

2. The medical instrument of claim 1, wherein the side of the second front fixing part is shaped to conform to the upper side and front side of the main body, so that the side of the second front fixing part is closely contacted with the upper side and front side of the main body.

3. The medical instrument of claim 1, wherein the at least one first rear fixing part is respectively disposed on a left and right side of the detachable lever.

4. The medical instrument of claim 1, wherein a rubber pad is disposed on at least one of the contacting portion and the at least one first rear fixing part, and the rubber pad is formed to face the main body.

5. The medical instrument of claim 1, wherein the at least one first rear fixing part is respectively disposed on a left and right side of the detachable lever.

6. The medical instrument of claim 1, wherein the detachable lever acts as a handle mounted on the rear portion of the main body.

7. The medical instrument of claim 1, wherein the second front fixing part comprises:
    a guide formed on a front portion of the desk;
    a location control part coupled with the guide and movable back and forth along the guide; and
    a latching part backwardly protruded from the location control part and closely contacting with an upper surface of the main body.

* * * * *